United States Patent
Tsao

(10) Patent No.: US 7,184,132 B2
(45) Date of Patent: Feb. 27, 2007

(54) INSPECTION METHOD AND APPARATUS OF LASER CRYSTALLIZED SILICONS

(75) Inventor: I-Chang Tsao, Hsinchu (TW)

(73) Assignee: AU Optronics Corp., Hsinchu (TW)

( * ) Notice: Subject to any disclaimer, the term of this patent is extended or adjusted under 35 U.S.C. 154(b) by 361 days.

(21) Appl. No.: 10/792,833

(22) Filed: Mar. 5, 2004

(65) Prior Publication Data

US 2005/0002016 A1    Jan. 6, 2005

(30) Foreign Application Priority Data

Jul. 1, 2003    (TW) ............................... 92118003 A

(51) Int. Cl.
*G01N 21/00*    (2006.01)
(52) U.S. Cl. ...................... 356/30; 356/72; 356/237.1; 438/16
(58) Field of Classification Search .................. 356/30, 356/72, 237.1; 438/16
See application file for complete search history.

(56) References Cited

U.S. PATENT DOCUMENTS 6,798,498 B2 *   9/2004   Wada et al. .................. 356/30
2003/0017658 A1 *   1/2003   Nishitani et al. ........... 438/149

FOREIGN PATENT DOCUMENTS

TW          536622       1/1991
WO       WO 01/61734 A1 *   8/2001

\* cited by examiner

*Primary Examiner*—F. L. Evans
(74) *Attorney, Agent, or Firm*—Troxell Law Office PLLC

(57) ABSTRACT

An inspection method and apparatus of laser crystallized silicons in the low-temperature poly Si (LTPS) process. The crystalline quality is inspected by using a visible light source to irradiate the surface of the poly Si and examining the variations of the reflected light caused by the protrusion arrangement at the surface of the poly Si. This method can be adopted on the poly Si samples prepared by the line scanning of the excimer laser annealing (ELA) technology.

20 Claims, 4 Drawing Sheets

INSPECTION METHOD AND APPARATUS OF LASER CRYSTALLIZED SILICONS

FIELD OF THE INVENTION

The present invention relates to an inspection method and apparatus of laser crystallized silicons and, more specifically, to an inspection method for synchronously monitoring the formation of laser crystallized silicons in the low-temperature poly Si (LTPS) process and an inspection apparatus using thereof.

BACKGROUND OF THE INVENTION

With the advance of techniques for manufacturing thin-film transistors, the liquid crystal displays (LCD) are widely applied in various electronic products, such as calculators, personal digital assistants (PDAs), watches, laptops, digital cameras, and mobile phones, etc. due to their advantages as smaller size, less weight, lower power consumption and no radiation. Furthermore, since manufacturers aggressively invest in research & development and employ large-scale fabricating equipment, the decreasing cost of production makes the TFT-LCD devices more popular.

Since the low-temperature poly Si (LTPS) thin film transistor LCDs are superior in resolution, brightness, size and anti-electromagnetic interferences, the LCD manufacturers are gradually focusing on such a technical field. Considering quality of films and requirements of mass production, an excimer laser annealing (ELA) is employed in the LTPS process. The excimer laser is used as a heat source and the laser light through the projection system produces laser beams with uniform energy distribution projected onto the a-Si structure on the substrate. After the a-Si structure on the substrate absorbs the energy of the excimer laser, the a-Si structure is transformed to be a poly Si structure. The entire annealing process is performed below 600° C. and a typical glass substrate or a plastic substrate can be used.

As mentioned in the above, in the application of the LTPS, the a-Si structure deposited on the substrate is irradiated and scanned by a laser beam to form laser crystallized silicons. The quality of the laser crystallized silicons has direct influences on the characteristics of various elements later formed. However, the current methods for inspecting the quality of the crystallized silicons on the substrate are not ideal. One is a method of scanning electron microscope (SEM) for examining the size, shape and distribution of the grains. Since the SEM method has to cut the substrate for sample analysis and needs a chemical pre-treatment, it cannot be directly employed on the production line and can only be used for sampling inspection due to the fact that it is destructive to the substrate. The other is a method of deep UV microscope for examining the arrangement of protrusions at the surface of the crystallized silicons. However, the deep UV microscope method can merely be used to inspect the crystallization of several microns on the substrate because it must magnify the sample to more than ten thousand times and it would take several days to inspect the whole substrate, and the equipment of the deep UV microscope method is complicated, delicate and at a high price.

Therefore, the improvements in the current inspection methods of the laser crystallized silicons in the LTPS process are urgently desired so as to provide a satisfactory inspection result of the laser crystallized silicons.

SUMMARY OF THE INVENTION

It is an object of the present invention to provide an inspection method of laser crystallized silicons applied in the low-temperature poly Si (LTPS) process. By the phenomenon of similar beam splitting-gratings caused by the protrusion arrangement at the surface of the crystallized silicons formed on an insulating substrate through the line scanning of the excimer laser annealing (ELA) technology, a simple and prompt method for examining the crystalline quality of the surface of the crystallized silicons is provided.

It is another object of the present invention to provide an inspection method for synchronously monitoring the formation of laser crystallized silicons in the low-temperature poly Si (LTPS) process. A visible light source for irradiating the surface of the crystallized silicons and a camera for catching the reflected light of the light source are employed in combination with an excimer laser annealing (ELA) machine of line scanning so as to monitor the crystallization at the surface of the crystallized silicons and to modify and adjust the laser energy of the excimer laser annealing (ELA) machine immediately whenever the abnormal crystallization is found.

It is still another object of the present invention to provide an inspection apparatus using the above-mentioned inspection method.

According to a first aspect of the present invention, an inspection method of laser crystallized silicons applied in the low-temperature poly Si (LTPS) process comprises the steps of using a visible light source such as a white or green light to irradiate the surface of the crystallized silicons on an insulating substrate, and examining the quality of the crystallization by variations of the light reflected by the protrusion arrangement at the surface of the crystallized silicons formed through the line scanning of the excimer laser annealing (ELA) technology. For instance, when the variations of the reflected light are large and obvious, stripes are distributed over the surface of the crystallized silicons and this represents a poor quality of crystallization.

According to a second aspect of the present invention, an inspection method for synchronously monitoring the formation of laser crystallized silicons in the low-temperature poly Si (LTPS) process is disclosed. This method includes the steps of performing an excimer laser annealing (ELA) technology in a line scanning manner to transform amorphous silicons on a substrate to crystallized silicons, synchronously using a visible light source to irradiate the surface of the crystallized silicons, examining the crystallization quality of the crystallized silicons by variations of the light reflected by the protrusion arrangement at the surface of the crystallized silicons, and monitoring whether the laser energy of the laser beam used in the ELA technology does not match the crystallization conditions of the amorphous silicons or the laser energy thereof is unstable. For instance, when the variations of the reflected light are large and obvious, stripes are distributed over the surface of the crystallized silicons and this represents a poor crystallization quality and the laser energy is unsuitable or unstable.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

A novel inspection method of laser crystallized silicons is provided in this invention. In the process for irradiating the amorphous silicons on an insulating substrate such as glass substrate with a laser beam through an excimer laser annealing (ELA) technology of line scanning to be crystallized, a visible light source such as a white light is used to irradiate the surface of the crystallized silicons, and the quality of the crystallization is examined by variations of the light reflected by the protrusion arrangement at the surface of the crystallized silicons. For instance, when the intensity of the reflected light is large and obvious, stripes are distributed over the surface of the crystallized silicons and this represents a poor quality of crystallization. Moreover, whether the laser energy of the laser beam used in the ELA technology does not match the crystallization conditions of the amorphous silicons or the laser energy thereof is unstable can also be monitored.

Refer to FIGS. 1A to 1C and FIGS. 2A to 2C, which are respectively atomic force microscope pictures and corresponding electronic microscope pictures of samples of the crystallized silicons, wherein the samples of the electronic microscope have been chemically treated to expose the grain boundary of the crystallized silicons so as to inspect the quality of crystallization.

Figure 1A:
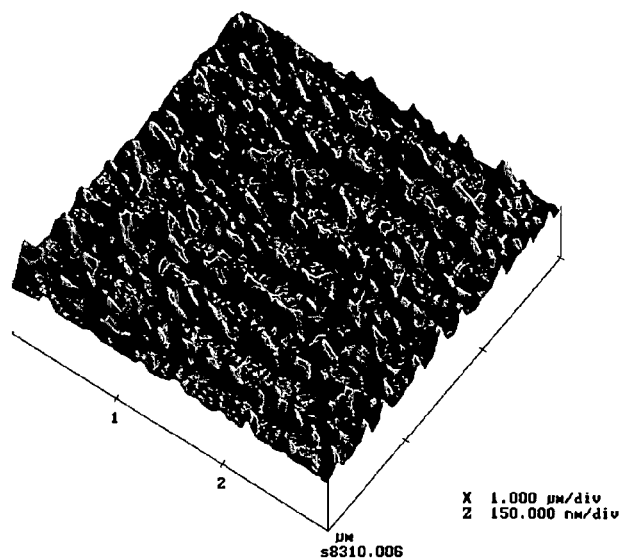
FIGS. 1A to 1C are atomic force microscope pictures of samples of the laser crystallized silicons of a glass substrate.
Figure 1B:
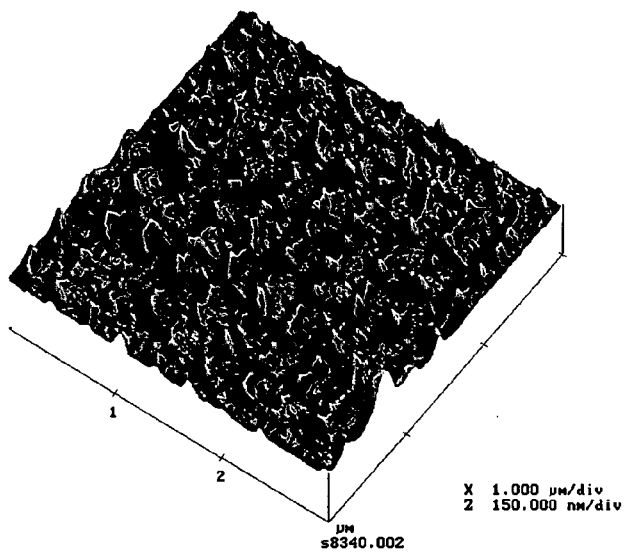
Figure 1C:
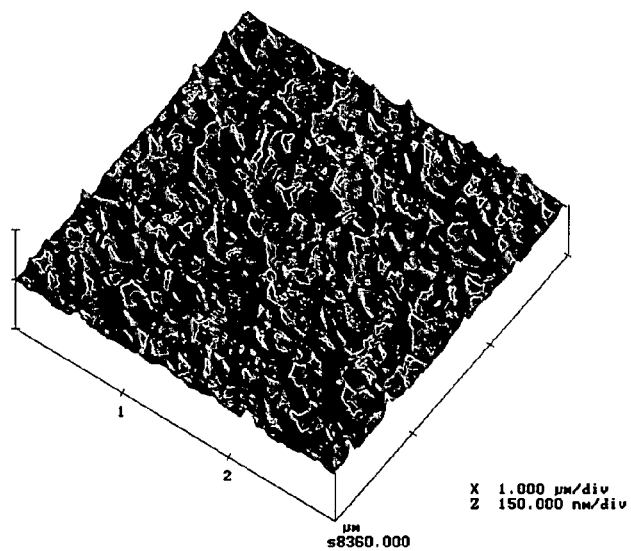
Figure 2A:
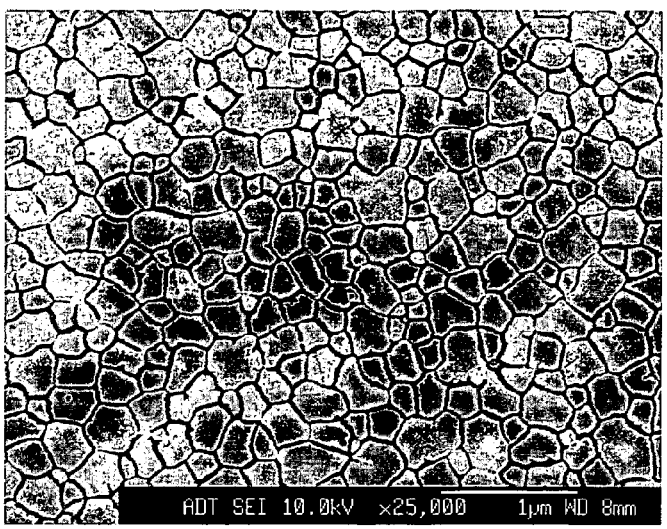
FIGS. 2A to 2C are corresponding electronic microscope pictures of the samples of the laser crystallized silicons as shown in FIGS. 1A to 1C.
Figure 2B:
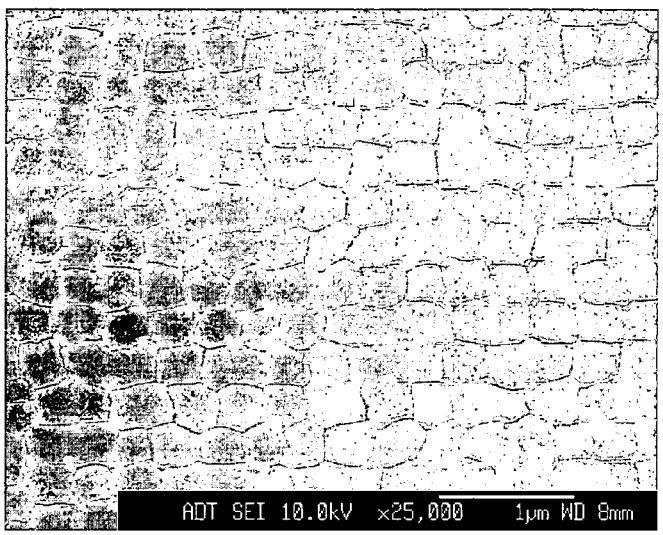
Figure 2C:
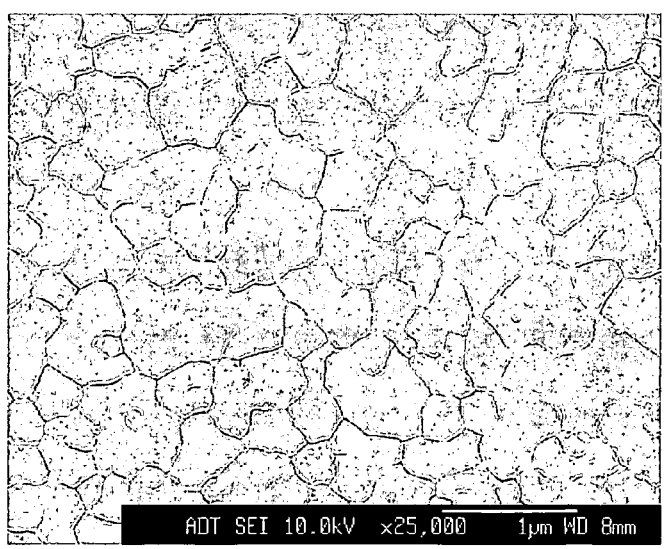

FIGS. 1A and 2A show the crystallization state of the insufficient laser energy. It is found that the protrusions at the surface of the crystallized silicons in FIG. 1A are in a random arrangement and that the grain boundary of the crystallized silicons in FIG. 2A is in disorder. When the laser energy is increased to be in optimal conjunction with the crystallization conditions of the amorphous silicons such as the thickness of the amorphous silicon film, the thickness of silicon oxide formed at the surface of the film and the ambience of laser crystallization, the crystallization state of a uniform and regular arrangement is formed, as shown in FIGS. 1B and 2B. However, when the laser energy goes beyond, the crystallization state of regularity disappears, as shown in FIGS. 1C and 2C.

According to long-term research and observation, it is found that the protrusions formed at the surface of the crystallized silicons are in a uniform and regular arrangement when the laser energy is in optimal conjunction with the crystallization conditions, wherein the direction of the arrangement is perpendicular to the scanning direction of the laser, and the space between two lines of the protrusions is about 2500–3300 nm, and the average angular distribution of the protrusions with respect to the plane of the film is at 70–80 degrees. Because of the uniform and regular protrusion arrangement formed at the surface of the crystallized silicons, the surface of the crystallized silicons has a function similar to beam splitting-gratings. When a white light source is used to irradiate the surface of the crystallized silicons about at a 10–85 degree angle of the plane of the substrate, preferably at a 15–30 degree angle, the optical path difference of the lights reflected by the regularly arranged protrusions at the surface of the crystallized silicons is calculated according to the formula to be 5394–5684 nm, which is exactly the wavelength of a green light. That is, the uniform and regular protrusion arrangement can results in the maximum constructive interference of a bright green light. Hence, when an observer looking within the irradiation angle range of the white light source, he/she will see that the surface of the crystallized silicons in the optimized crystallization appears green.

Figure 3:
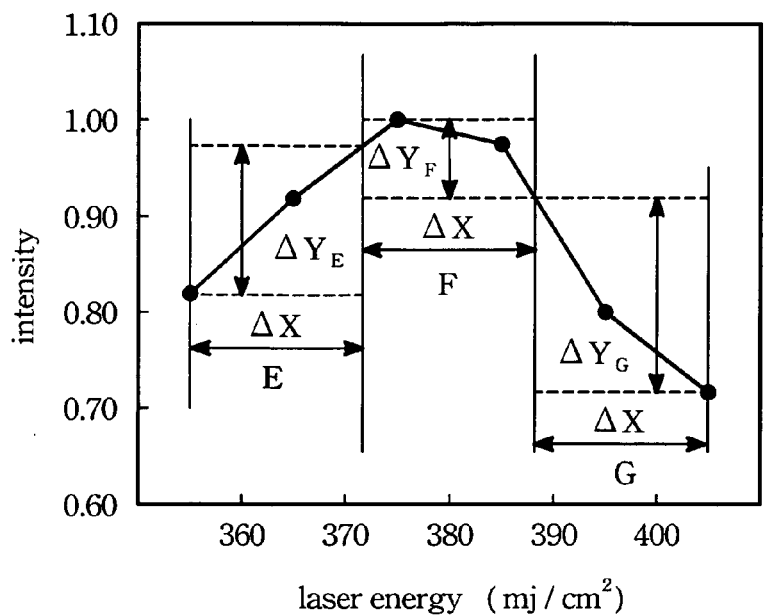
FIG. 3 is a diagram showing the relation between the normalized intensity of the reflected light and the amount of the laser energy in accordance with this invention.

FIG. 3 shows the relation between the intensity of the reflected green light and the amount of the laser energy. When the laser energy is appropriate, as shown in the F region of FIG. 3, the intensity variation of the reflected green light (the value of $\Delta Y/\Delta X$) is small although a certain of variation will occur because of the discontinuous output of the ELA laser light itself. However, when the laser energy is unsuitable, as shown in the E region of insufficient laser energy and the G region of excessive laser energy of FIG. 3, the intensity variation of the reflected green light with respect to the same laser energy in the F region is large. Under such circumstance, the intensity variations of the reflected green light at the surface of the crystallized silicons of different positions on the substrate are so obvious that stripes are fully distributed at the surface of the crystallized silicons. In other words, when the surface of the crystallized silicons is irradiated by a white light source about at an 10–85 degree angle with respect to the plane of the substrate, it can be concluded that the laser energy is inappropriate if an observer within the irradiation angle range of the white light source sees the stripes showing at the surface of the crystallized silicons. Furthermore, the best plane orientation to observe whether the stripes appear at the surface of the crystallized silicons is perpendicular to or parallel with the scanning direction of the laser.

Figure 4:
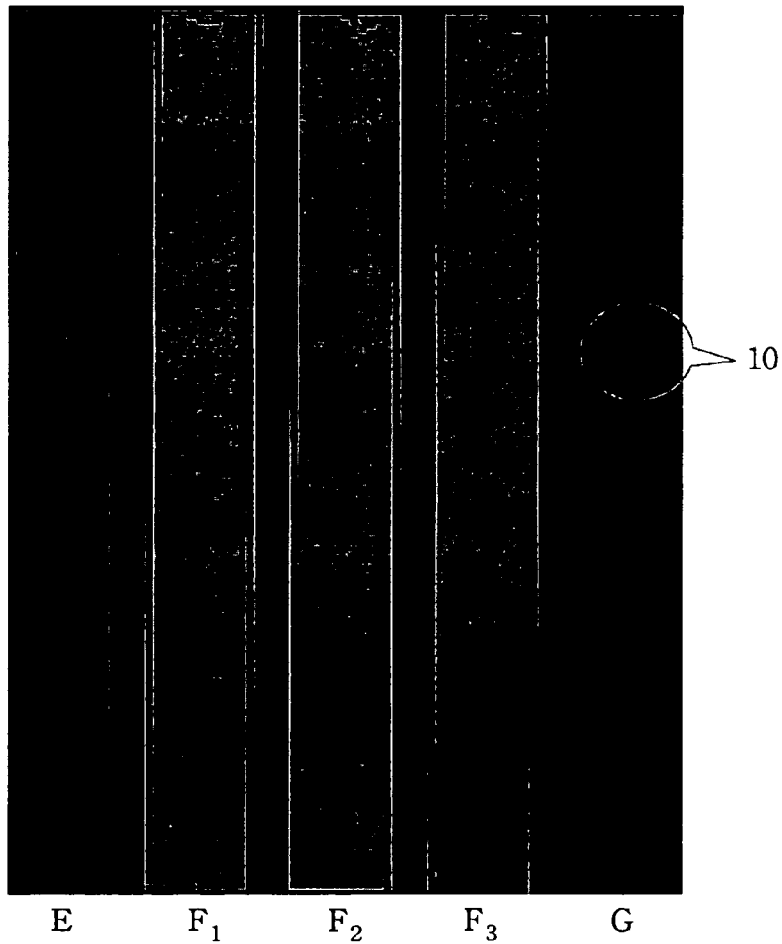
FIG. 4 shows a picture of the crystallized silicon regions on a glass substrate formed by different amounts of laser energy after irradiated by a white light, taken by the camera in accordance with this invention.

Because of the progress in the modern mage technology, a camera such as a CCD lens with a tens mm resolution may be used in replacement for the observer's eyes to catch the images of the reflected light. FIG. 4 shows a picture of the crystallized silicon regions on a glass substrate formed by different amounts of laser energy after irradiated by a white light, taken by the camera, wherein the laser energy is insufficient in the E region, the laser energy is appropriate in the $F_1$, $F_2$ and $F_3$ regions and the laser energy is excessive in the G region. As shown in FIG. 4, stripes are fully distributed at the surface of the crystallized silicons in the E region of insufficient laser energy and the G region of excessive laser energy.

Figure 5:
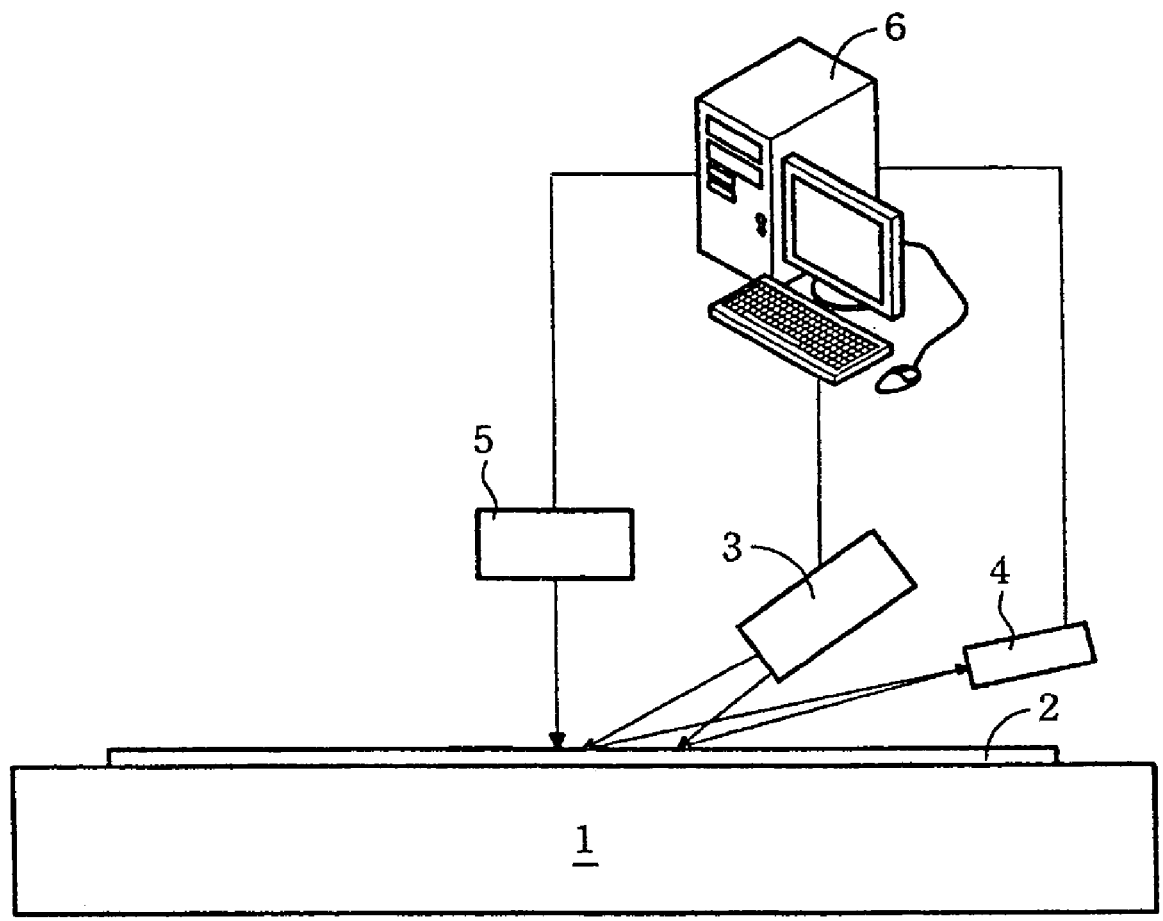
FIG. 5 is a schematic instrument construction diagram of the inspection method of laser crystallized silicons in accordance with this invention.

Hence, a simple and rapid inspection method of laser crystallized silicons is designed according to the above-mentioned research and discovery. As shown in FIG. 5, a visible light source 3 is used to irradiate the surface of the crystallized silicons of a substrate 2 disposed on a platform 1 about at a 10–85 degree angle with respect to the plane of the substrate, and a camera 4 is used to catch the reflected images of the surface of the crystallized silicons of the whole substrate, within the irradiation angle range of the light source 3. The captured images are then inputted into a computer 6 for treatment and analysis. For instance, by analyzing the uniformity, contrast or gray scale of the light intensity of the image at a selected region, the crystallization state of the selected region can be obtained to facilitate process monitoring.

The equipment necessary for performing the inspection method of laser crystallized silicons in this invention is merely a visible light source and a camera, and can be combined with the excimer laser annealing (ELA) machine 5 to design an inspection apparatus for synchronously monitoring the formation of laser crystallized silicons in the low-temperature poly Si (LTPS) process so as to modify and adjust the laser energy of the ELA machine 5 immediately whenever the abnormal crystallization is monitored. For the inspection method of laser crystallized silicons in this invention, it takes only 5–10 seconds to capture the reflected images at the surface of the crystallized silicons on the whole about 1 m² substrate and to analyze them with a computer software. In addition, the inspection method of laser crystallized silicons in this invention can not only examine the situation that the laser energy is inappropriate to the crystallization conditions of the amorphous silicons, but also examine the non-uniform crystallization resulted from the unstable laser energy, i.e. the situation that the laser energy is accurately set but unstably outputted.

Therefore, comparing with the conventional SEM method and deep UV method, the method provided in this invention is more rapid, convenient and economical, and is suitable for process monitoring.

As is understood by a person skilled in the art, the foregoing embodiment of the present invention is an illustration of the present invention rather than limiting the present invention. It is intended to cover various modifications and similar arrangements included within the spirit and scope of the appended claims, the scope of which should be accorded the broadest interpretation so as to encompass all such modifications and similar structure.

What is claimed is:

1. An inspection method of laser crystallized silicons applied in the low-temperature poly Si (LTPS) process, said inspection method comprising:
   using a visible light source to irradiate a surface of said crystallized silicons into which amorphous silicons on an insulating substrate are transformed through the line scanning of an excimer laser annealing (ELA) technology; and
   using a camera for capturing the reflected images of the surface of said crystallized silicons after irradiated by said light source to examine the quality of the crystallization by variations of the light reflected by the arrangement of protrusions at the surface of said crystallized silicons.

2. The inspection method of claim 1, wherein when the variations of the reflected light are large and obvious, stripes are distributed over the surface of said crystallized silicons and this represents a poor quality of crystallization.

3. The inspection method of claim 1, wherein said visible light source irradiates the surface of said crystallized silicons about at a 10–85 degree angle with respect to the plane of said substrate.

4. The inspection method of claim 3, wherein said visible light source irradiates the surface of said crystallized silicons about at a 15–30 degree angle with respect to the plane of said substrate.

5. The inspection method of claim 1, wherein said visible light source is a white light.

6. The inspection method of claim 1, wherein said visible light source is a green light.

7. An inspection method for synchronously monitoring the formation of laser crystallized silicons in the low-temperature poly Si (LTPS) process, said inspection method comprising:
   performing an excimer laser annealing (ELA) technology in a line scanning manner to transform amorphous silicons on an insulating substrate to said crystallized silicons;
   synchronously using a visible light source to irradiate a surface of said crystallized silicons;
   using a camera for capturing the reflected images of the surface of said crystallized silicons after irradiated by said light source to examine the crystallization quality of said crystallized silicons by variations of the light reflected by the arrangement of protrusions at the surface of said crystallized silicons; and monitoring whether the laser energy of the laser beam used in the ELA technology does not match the crystallization conditions of said amorphous silicons or the laser energy thereof is unstable.

8. The inspection method of claim 7, wherein when the variations of the reflected light are large and obvious, stripes are distributed over the surface of said crystallized silicons and this represents a poor crystallization quality and the laser energy is inappropriate or unstable.

9. The inspection method of claim 7, wherein said visible light source irradiates the surface of said crystallized silicons about at a 10–85 degree angle with respect to the plane of said substrate.

10. The inspection method of claim 7, wherein said visible light source is a white light.

11. An inspection apparatus of laser crystallized silicons applied in the low-temperature poly Si (LTPS) process, said inspection apparatus comprising:
    an excimer laser annealing (ELA) machine for irradiating amorphous silicons on an insulating substrate with a laser beam in a line scanning manner to be transformed into said crystallized silicons;
    a visible light source for irradiating the surface of said crystallized silicons on said substrate; and
    a camera for capturing the reflected images of the surface of said crystallized silicons after irradiated by said light source to examine the crystallization state of the surface of said crystallized silicons.

12. The inspection apparatus of claim 11, further comprising a computer for receiving and analyzing said images captured by said camera so as to monitor the crystallization state of a selected region at the surface of said crystallized silicons and to make immediate process adjustments.

13. The inspection apparatus of claim 12, wherein the uniformity, contrast and gray scale of the light intensity of said images at said selected region are analyzed to monitor the crystallization state of said selected region and to make immediate adjustments in the laser energy of said laser beam.

14. The inspection apparatus of claim 11, wherein said camera captures the reflected images of the surface of said crystallized silicons on the whole substrate after irradiated by said light source.

15. The inspection apparatus of claim 11, wherein said visible light source irradiates the surface of said crystallized silicons about at a 10–85 degree angle with respect to the plane of said substrate.

16. The inspection apparatus of claim 11, wherein said visible light source is a white light.

17. The inspection apparatus of claim 11, wherein said visible light source is a green light.

18. The inspection apparatus of claim 15, wherein said camera is vertically oriented within the irradiation angle range of said visible light source.

19. The inspection apparatus of claim 11, wherein said camera is horizontally oriented in the direction perpendicular to that of the line scanning of said laser beam.

20. The inspection apparatus of claim 11, wherein said camera is horizontally oriented in the direction parallel to that of the line scanning of said laser beam.

* * * * *